United States Patent
Wu et al.

(10) Patent No.: US 10,045,728 B2
(45) Date of Patent: Aug. 14, 2018

(54) KIDNEY GLOMERULI MEASUREMENT SYSTEMS AND METHODS

(71) Applicants: Teresa Wu, Gilbert, AZ (US); Min Zhang, Tempe, AZ (US)

(72) Inventors: Teresa Wu, Gilbert, AZ (US); Min Zhang, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 221 days.

(21) Appl. No.: 15/082,095

(22) Filed: Mar. 28, 2016

(65) Prior Publication Data

US 2016/0206235 A1    Jul. 21, 2016

Related U.S. Application Data

(63) Continuation of application No. PCT/US2014/059545, filed on Oct. 7, 2014.
(Continued)

(51) Int. Cl.
*G06K 9/00* (2006.01)
*A61B 5/20* (2006.01)
(Continued)

(52) U.S. Cl.
CPC ............ *A61B 5/201* (2013.01); *A61B 5/055* (2013.01); *A61B 5/7225* (2013.01);
(Continued)

(58) Field of Classification Search
CPC .............. G06T 7/0012; G06T 7/11; G06T 2207/10081; G06T 2207/10088; G06T 2207/10072; G06T 2207/30004; G06T 2207/30084; G06T 7/344; G06T 2200/04; G06T 5/00; G06T 5/002; G06T 5/003;
(Continued)

(56) References Cited

U.S. PATENT DOCUMENTS

| | | | |
|---|---|---|---|
| 2004/0151356 A1* | 8/2004 | Li | G06K 9/527 382/131 |
| 2005/0119829 A1 | 6/2005 | Bishop et al. | |

(Continued)

OTHER PUBLICATIONS

Frangi, Alejandro F., et al. "Multiscale vessel enhancement filtering." International Conference on Medical Image Computing and Computer-Assisted Intervention. Springer Berlin Heidelberg, 1998.*

(Continued)

*Primary Examiner* — Li Liu
(74) *Attorney, Agent, or Firm* — Snell & Wilmer L.L.P.

(57) ABSTRACT

Methods and systems for identifying blobs, for example kidney glomeruli, are disclosed. A raw image may be smoothed via a difference of Gaussians filter, and a Hessian analysis may be conducted on the smoothed image to mark glomeruli candidates. Exemplary candidate features are identified, such as average intensity $A_T$, likelihood of blobness $R_T$, and flatness $S_T$. A clustering algorithm may be utilized to post prune the glomeruli candidates.

10 Claims, 13 Drawing Sheets

Related U.S. Application Data

(60) Provisional application No. 61/887,668, filed on Oct. 7, 2013.

(51) Int. Cl.
*A61B 5/055* (2006.01)
*G06T 7/00* (2017.01)
*A61B 5/00* (2006.01)
*G06T 7/11* (2017.01)

(52) U.S. Cl.
CPC .......... *A61B 5/7264* (2013.01); *G06T 7/0012* (2013.01); *G06T 7/11* (2017.01); *A61B 2576/02* (2013.01); *G06T 2207/10088* (2013.01); *G06T 2207/30084* (2013.01)

(58) Field of Classification Search
CPC .... G06T 7/35; G06T 7/45; G06T 7/73; G06K 9/6226
See application file for complete search history.

(56) References Cited

U.S. PATENT DOCUMENTS

| | | | | |
|---|---|---|---|---|
| 2005/0244042 | A1* | 11/2005 | Sirohey | G06T 7/0012 382/131 |
| 2007/0036409 | A1* | 2/2007 | Valadez | G06T 7/0012 382/128 |
| 2007/0133894 | A1* | 6/2007 | Kiraly | G06K 9/4609 382/260 |
| 2008/0100612 | A1* | 5/2008 | Dastmalchi | A61B 3/102 345/418 |
| 2008/0317314 | A1 | 12/2008 | Schwartz et al. | |
| 2009/0005693 | A1 | 1/2009 | Brauner et al. | |
| 2009/0122060 | A1* | 5/2009 | Porat | G06T 7/11 345/424 |
| 2011/0044524 | A1 | 2/2011 | Wang et al. | |
| 2011/0293157 | A1* | 12/2011 | Ye | G06K 9/6226 382/131 |
| 2012/0155734 | A1* | 6/2012 | Barratt | G06T 7/344 382/131 |
| 2012/0294502 | A1* | 11/2012 | Chan | G06T 7/0012 382/131 |
| 2013/0022548 | A1 | 1/2013 | Bennett | |
| 2013/0230230 | A1 | 9/2013 | Ajemba et al. | |
| 2013/0329972 | A1* | 12/2013 | Zhang | G06T 5/00 382/128 |
| 2014/0270436 | A1* | 9/2014 | Dascal | G06T 7/11 382/130 |
| 2015/0359475 | A1 | 12/2015 | Bennett et al. | |
| 2016/0005170 | A1 | 1/2016 | Thiagarajan et al. | |
| 2016/0189373 | A1* | 6/2016 | Park | A61B 6/032 382/131 |

OTHER PUBLICATIONS

Corduneanu, Adrian, and Christopher M. Bishop. "Variational Bayesian model selection for mixture distributions." Artificial intelligence and Statistics. vol. 2001. Waltham, MA: Morgan Kaufmann, 2001.*

S.C. Beeman et al. "Measuring Glomerular Number and Size in Perfused Kidneys using MRI", American Journal of Physiology Renal Physiology, vol. 300, No. 6, pp. F1454-F1457, 2011.

S.C. Beeman et al., "MRI-based Glomerular Morphology and Pathology in Whole Human Kidneys", American Journal of Physiology Renal Physiology, vol. 306, No. 11, pp. F1381-F1390, 2014.

M. Zhang et al. "Small Blob Identification in Medical Images Using Regional Features From Optimum Scale", IEEE Transactions on Biomedical Engineering, vol. 62, No. 4, pp. 1051-1062, Apr. 2015.

M. Zhang et al., "Efficient Small Blob Detection Based on Local Convexity, Intensity and Shape Information", IEEE Transactions on Medical Imaging, vol. 35, No. 4, pp. 1127-1137, Apr. 2016.

E.J. Baldelomar et al., "Phenotyping by Magnetic Resonance Imaging Nondestructively Measures Glomerular Number and Volume Distribution in Mice with and without Nephron Reduction", Kidney International, vol. 89, No. 2, pp. 498-505, 2016.

S.P. Sourbron et al., "MRI-Measurement of Perfusion and Glomerular Filtration in the Human Kidney with a Separable Compartment Model", Investigative Radiology, vol. 43 No. 1, pp. 40-48, Jan. 2008.

L. Annet et al., "Glomerular Filtration Rate: Assessment with Dynamic Contrast-Enhanced MRI and a Cortical-Compartment Model in the Rabbit Kidney", Journal of Magnetic Resonance Imaging, vol. 20, No. 5, pp. 843-849, 2004.

L. Hermoye et al., "Calculation of the Renal Perfusion and Glomerular Filtration Rate From the Renal Impulse Response Obtained With MRI", Magnetic Resonance in Medicine, vol. 51, No. 5, pp. 1017-1025, 2004.

P.S. Tofts et al., "Precise Measurement of Renal Filtration and Vascular Parameters Using a Two-Compartment Model for Dynamic Contrast-Enhanced MRI of the Kidney Gives Realistic Normal Values", European Radiology, vol. 22, No. 6, pp. 1320-1330, 2012.

I. Mendichovszky et al., "How Accurate is Dynamic Contrast-Enhanced MRI in the Assessment of Renal Glomerular Filtration Rate? A Critical Appraisal", Journal of Magnetic Resonance Imaging, vol. 27, No. 4, pp. 925-931, 2008.

E. Eikefjord et al., "Use of 3D DCE-MRI for the Estimation of Renal Perfusion and Glomerular Filtration Rate: An Intrasubject Comparison of FLASH and KWIC With a Comprehensive Framework for Evaluation", American Journal of Roentgenology, vol. 204, No. 3, pp. W273-W281, Mar. 2015.

K.M. Bennett et al., "The Emerging Role of MRI in Quantitative Renal Glomerular Morphology"American Journal of Physiology Renal Physiology, vol. 304, No. 10, pp. F1252-F1257, 2013.

Y.-D. Zhang et al., "Feasibility Study of High-Resolution DCE-MRI for Glomerular Filtration Rate (GFR) Measurement in a Routine Clinical Modal", Magnetic Resonance Imaging, vol. 33, No. 8, pp. 978-983, 2015.

M. Zeng et al., "Measurement of Single-Kidney Glomerular Filtration Function from Magnetic Resonance Perfusion Renography", European Journal of Radiology, vol. 84, No. 8, pp. 1419-1423, 2015.

K. Bennett et al., "MRI Quantification of Single Glomerular Function", Meeting Abstract, American Journal of Kidney Diseases, vol. 53, No. 4, 25, p. A29, 2009.

V. Finkielstein et al., "Single Kidney Glomerular Filtration Rate (GFR) Based on Dynamic Contrast Magnetic Resonance Imaging (MRI) and a Multicompartmental Model", Journal of the American Society of Nephrology, vol. 14, p. 614A, SU-P0365, 2003.

M. Zhang, "Small Blob Detection in Medical Images", PhD Thesis, Arizona State University, May 2015.

W. E. Hoy et al., "Nephron Number, Glomerular Volume, Renal Disease and Hypertension," Current Opinion in Nephrology and Hypertension, vol. 17, No. 3, pp. 258-265, 2008.

J.F Bertram et al., "Total Numbers of Glomeruli and Individual Glomerular Cell Types in the Normal Rat Kidney", Cell and Tissue Research, vol. 270, No. 1, pp. 37-45, 1992.

L. A. Cullen-McEwen et al., "Estimating Total Nephron Number in the Adult Kidney Using the Physical Disector/Fractionator Combination", Methods in Molecular Biology, vol. 886, pp. 333-350, 2012.

J. F. Bertram, "Analyzing Renal Glomeruli with the New Stereology", International Review of Cytology, W. J. Kwang and J. Jonathan, eds., pp. 111-172: Academic Press, 1995.

K. M. Bennett et al., "MRI of the Basement Membrane Using Charged Nanoparticles as Contrast Agents", Magnetic Resonance in Medicine, vol. 60, No. 3, pp. 564-574, 2008.

F. Meyer, "Topographic Distance and Watershed Lines", Signal processing, vol. 38, No. 1, pp. 113-125, 1994.

(56) References Cited

OTHER PUBLICATIONS

Y. Al-Kofahi et al., "Improved Automatic Detection and Segmentation of Cell Nuclei in Histopathology Images", IEEE Transactions on Biomedical Engineering, vol. 57, No. 4, pp. 841-852, Apr. 2010.
E. Bernardis et al., "Finding Dots: Segmentation as Popping Out Regions from Boundaries", in Proceedings of the IEEE Conference on Computer Vision and Pattern Recognition (CVPR), pp. 199-206, 2010.
C. Couprie et al., "Power Watersheds: A New Image Segmentation Framework Extending Graph Cuts, Random Walker and Optimal Spanning Forest", in Proceedings of the IEEE 12th International Conference on Computer Vision (ICCV), pp. 731-738, 2009.
C. Russell, et al., "Using the Pn Potts Model with Learning Methods to Segment Live Cell Images," in Proceedings of the IEEE 11th International Conference on Computer Vision (ICCV), 2007, pp. 1-8, 2007.
H. Kong et al., "Partitioning Histopathological Images: An Integrated Framework for Supervised Color-Texture Segmentation and Cell Splitting," IEEE Transactions on Medical Imaging, vol. 30, No. 9, pp. 1661-1677, Sep. 2011.
E. Bernardis et al., "Segmentation Subject to Stitching Constraints: Finding Many Small Structures in a Large Image," in Procceedings of the International Conference on Medical Image Computing and Computer Assisted Intervention, pp. 119-126, Sep. 2010.
F. Yi et al., "White Blood Cell Image Segmentation Using On-line Trained Neural Network," in Proceedings of the 2005 IEEE, Engineering in Medicine and Biology 27th Annual Conference, pp. 6476-6479, Sep. 2005.
K. Nandy et al., "Automatic Segmentation and Supervised Learning-based Selection of Nuclei in Cancer Tissue Images," Cytometry Part A, vol. 81A, No. 9, pp. 743-754, 2012.
N. Harder et al., "Automated Recognition of Mitotic Patterns in Fluorescence Microscopy Images of Human Cells," in Proceedings of the 3rd IEEE International Symposium on Biomedical Imaging: Nano to Macro, pp. 1016-1019, 2006.
J. Kong et al., "Computer-Aided Evaluation of Neuroblastoma on Whole-Slide Histology Images: Classifying Grade of Neuroblastic Differentiation," Pattern Recognition, vol. 42, No. 6, pp. 1080-1092, 2009.
N. Badshah, et al., "Multigrid Method for the Chan-Vese Model in Variational Segmentation," Communications in Computational Physics, vol. 4, No. 2, pp. 294-316, 2008.
T. F. Chan et al., "Active Contours Without Edges," IEEE Transactions on Image Processing, vol. 10, No. 2, pp. 266-277, Feb. 2001.
C. Xu et al., "Snakes, Shapes, and Gradient Vector Flow," IEEE Transactions on Image Processing, vol. 7, No. 3, pp. 359-369, Mar. 1998.
S. K. Nath et al., "Cell Segmentation Using Coupled Level Sets and Graph-Vertex Coloring," in Proceedings of the International Conference on Medical Image Computing and Computer-Assisted Intervention(MICCAI), pp. 101-108, 2006.
O. Dzyubachyk et al., "Advanced Level-Set-Based Cell Tracking in Time-Lapse Fluorescence Microscopy," IEEE Transactions on Medical Imaging, vol. 29, No. 3, pp. 852-867, Mar. 2010.
G. Bertrand, "On Topological Watersheds," Journal of Mathematical Imaging and Vision, vol. 22, No. 2-3, pp. 217-230, 2005.
J. M Sharif et al., "Red Blood Cell Segmentation Using Masking and Watershed Algorithm: A Preliminary Study," in Proceedings of the 2012 International Conference on Biomedical Engineering (ICoBE), pp. 258-262, Feb. 2012.
H.-H. Lin et al., "Cell Segmentation and NC Ratio Analysis of Third Harmonic Generation Virtual Biopsy Images Based on Marker-Controlled Gradient Watershed Algorithm," in Proceedings of the IEEE International Symposium on Circuits and Systems (ISCAS), pp. 101-104, 2012.
C. F. Koyuncu et al., "Smart Markers for Watershed-Based Cell Segmentation," PLOS ONE, vol. 7, Issue 11, e48664, Nov. 2012.
J. Cousty et al., "Watershed Cuts: Minimum Spanning Forests and the Drop of Water Principle," IEEE Transactions on Pattern Analysis and Machine Intelligence, vol. 31, No. 8, pp. 1362-1374, Aug. 2009.
E. Bernardis et al., "Pop Out Many Small Structures from a Very Large Microscopic Image," Medical Image Analysis, vol. 15, No. 5, pp. 690-707, 2011.
N. Xu et al., "Object Segmentation Using Graph Cuts Based Active Contours," Science Direct, Computer Vision and Image Understanding, vol. 107, No. 3, pp. 210-224, 2007.
Q. Wen et al., "A Delaunay Triangulation Approach for Segmenting Clumps of Nuclei," in Proceedings of the IEEE International Symposium on Biomedical Imaging: From Nano to Macro, pp. 9-12, 2009.
H. Wang et al., "Clump Splitting via Bottleneck Detection and Shape Classification," Pattern Recognition, Elsevier Ltd., vol. 45, No. 7, pp. 2780-2787, 7, 2012.
M. Heilmann et al., "Quantification of Glomerular Number and Size Distribution in Normal Rat Kidneys Using Magnetic Resonance Imaging," Nephrology Dialysis Transplantation, vol. 27, No. 1, pp. 100-107, Jan. 1, 2012.
Y. Wang et al., "Shape Analysis with Conformal Invariants for Multiply Connected Domains and its Application to Analyzing Brain Morphology," in Proceedings of the IEEE Conference on Computer Vision and Pattern Recognition (CVPR), pp. 202-209, 2009.
P. Szeptycki et al., "Conformal Mapping-Based 3D Face Recognition," in Proceedings of the Fifth International Symposium on 3D Data Processing, Visualization and Transmission, pp. 1-8, 2010.
International Search Report and the Written Opinion dated Jan. 22, 2015 in International Application No. PCT/US2014/059545.
K. Mikolajczyk et al. "Scale & Affine Invariant Interest Point Detectors," International Journal of Computer Vision, vol. 60, No. 1, pp. 63-86, 2004.
G. Kindlmann et al., "Curvature-Based Transfer Functions for Direct Volume Rendering: Methods and Applications", in Proceedings of the 14th IEEE Visualization Conference (VIS'03), pp. 513-520, 2003.
H. Kong et al., "A Generalized Laplacian of Gaussian Filter for Blob Detection and its Applications," IEEE Transactions on Cybernetics, vol. 43, No. 6, pp. 1719-1733, 2013.
J. P. Bergeest et al., "Efficient Globally Optimal Segmentation of Cells in Fluorescence Microscopy Images Using Level Sets and Convex Energy Functionals," Medical Image Analysis, Elsevier Ltd., vol. 16, No. 7, pp. 1436-1444, 2012.
J.-P. Bonvalet et al., "Compensatory Renal Hypertrophy in Young Rats: Increase in the Number of Nephrons," Kidney International, vol. 1, No. 6, pp. 391-396, 1972.
D. Danon et al., "Use of Cationized Ferritin as a Label of Negative Charges on Cell Surfaces," Journal of Ultrastructure Research, vol. 38, No. 5, pp. 500-510, 1972.
M. G. Uberti et al., "A Semi-Automatic Image Segmentation Method for Extraction of Brain Volume from In Vivo Mouse Head Magnetic Resonance Imaging Using Constraint Level Sets," Journal of Neuroscience Methods, Elsevier, Ltd., vol. 179, No. 2, pp. 338-344, 2009.
L. Xie et al., "Magnetic Resonance Histology of Age-Related Nephropathy in the Sprague Dawley Rat," Toxicologic Pathology, vol. 40, No. 5, pp. 764-778, 2012.
S. C. Beeman et al., "Toxicity, Biodistribution, and Ex Vivo MRI Detection of Intravenously Injected Cationized Ferritin," Magnetic Resonance in Medicine, vol. 69, 584 No. 3, pp. 853-861, 2013.
M. Zhang et al.,"An Efficient Framework for Automated Kidney Glomerular Segmentation in 3D MRI After Injection of Cationic Nanoparticles," Available at: http://swag.engineering.asu.edu/AM-MIL-2013-01.pdf (Accessed Jun. 6, 2016).
D. Tomar et al., "Nucleo-Cytophasmic Trafficking of TRIM8, a Novel Oncogene, is Involved in Positive Regulation of TNF Induced NF-κB Pathway," PLOS One, vol. 7, Issue 11, e48662, Nov. 2012.

* cited by examiner

KIDNEY GLOMERULI MEASUREMENT SYSTEMS AND METHODS

CROSS-REFERENCE TO RELATED APPLICATIONS

This application is a continuation of PCT Application No. PCT/US2014/059545 filed on Oct. 7, 2014 and entitled "KIDNEY GLOMERULI MEASUREMENT SYSTEMS AND METHODS". PCT Application No. PCT/US2014/059545 claims priority to, and the benefit of, U.S. Provisional Application Ser. No. 61/887,668 filed on Oct. 7, 2013 and entitled "KIDNEY GLOMERULI MEASUREMENT SYSTEMS AND METHODS". Each of the above applications is hereby incorporated by reference in their entirety.

FEDERALLY SPONSORED RESEARCH OR DEVELOPMENT

This invention was made with government support under grant number R21-DK091722 awarded by the National Institute of Health. The government has certain rights in the invention.

TECHNICAL FIELD

The present disclosure relates to image processing, and specifically to systems and methods to measure glomeruli in the kidneys.

BACKGROUND

The glomeruli of the kidney perform the key role of blood filtration. Each functioning glomerulus consists of a tuft of capillaries and several types of cells, and is surrounded by a Bowman's capsule forming the corpuscle. The number of glomeruli in a kidney is correlated with susceptibility to chronic kidney and cardiovascular disease, driving interest in technology to measure glomerular morphology. Cationic ferritin nanoparticles have been used to target, image, and count individual glomeruli in the whole kidney with magnetic resonance imaging (MRI). Accumulated nanoparticles create spots in MR images at each glomerulus. However, previous techniques have been unable to perform fast, reliable measurements of glomeruli in the image. Accordingly, improved techniques are desirable.

BRIEF DESCRIPTION OF THE DRAWINGS

With reference to the following description and accompanying drawings.

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the present disclosure.

Prior techniques were unable to perform fast, reliable measurements of kidney glomeruli in a 3 dimensional (3D) image. Traditionally, glomeruli, and thereby nephrons, have been counted using stereological or morphometric techniques applied to histological sections. The gold standard method is known as the dissector/fractionator stereological technique. While this technique provides good estimates of total glomerular number, it is limited to studies of kidneys obtained at autopsy, as representative 3D samples from the kidney are required. Recently, superparamagnetic, cationic ferritin (CF) nanoparticles have been developed as contrast agents for magnetic resonance imaging (MRI). CF binds to anionic proteoglycans in the glomerular basement membrane after intravenous injection, and the accumulation of CF may be detected with T2*-weighted MRI in 3D. This technique can be used to detect, measure, and count every glomerulus in the whole kidney ex vivo and in vivo. While exciting, the widespread use of this technique for preclinical and clinical studies is compromised by the lack of image processing tools to reliably and accurately segment glomeruli in the magnetic resonance (MR) images. In accordance with principles of the present disclosure, a computational pipeline to process 2D and/or 3D MRI images to accurately, and robustly count glomeruli in whole kidney in vivo is presented.

In accordance with principles of the present disclosure, in various exemplary embodiments an image processing system for measuring glomeruli in a kidney comprises a suitable computing device configured for image processing. In an exemplary embodiment, an image processing system comprises a high-performance workstation (e.g., configured with a multi-core processor such as a six-core XEON brand processor supplied by Intel Corporation) having a suitable amount of RAM (e.g., 4 GB or more) and a suitable graphics card (e.g., a workstation-class graphics card supplied by NVIDIA Corporation, Advanced Micro Devices, or similar).

Figure 1:
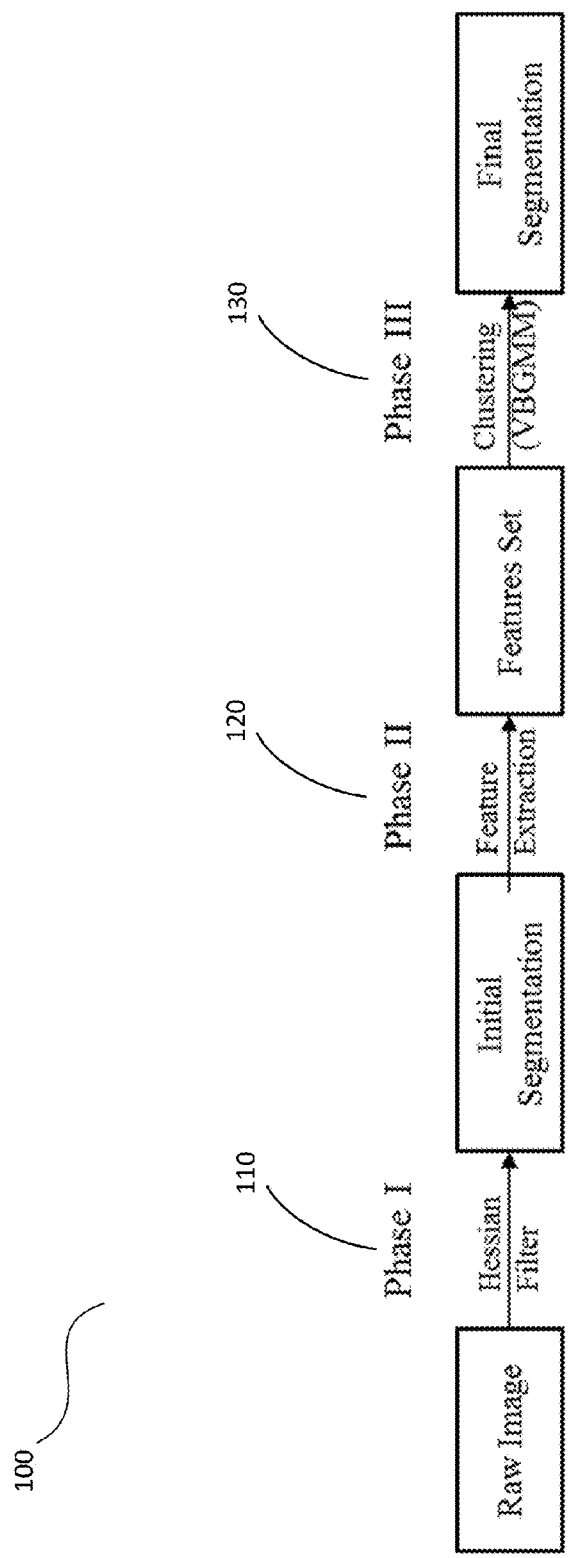
FIG. 1 illustrates a flow chart of an exemplary Hessian based multi-feature clustering method (HmFC) 100 in accordance with various exemplary embodiments.
Figure 2:
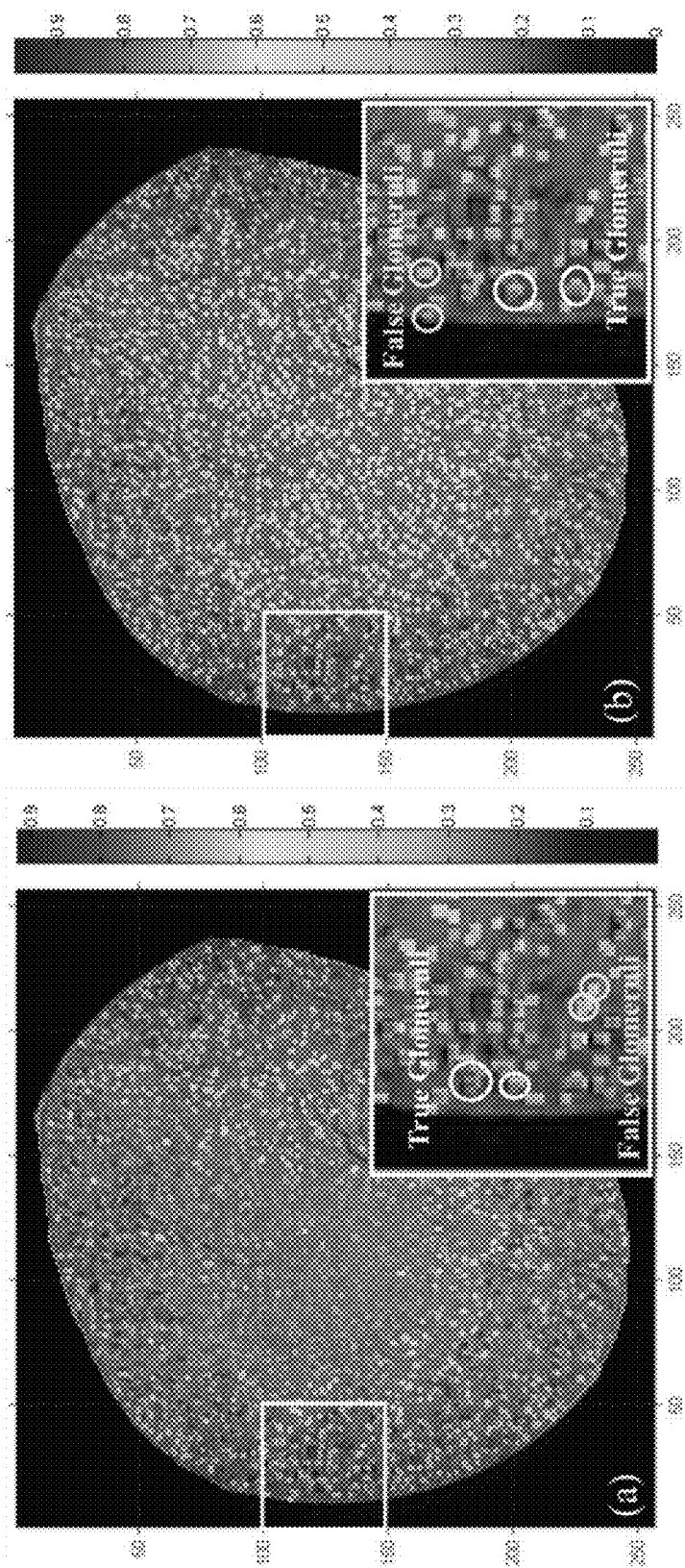
FIG. 2 illustrates glomeruli candidate regions of an original rat kidney image, showing (a) AI measures of candidate regions after being standardized to [0,1], and (b) Div measures of candidate regions after being standardized to [0,1], all in accordance with various exemplary embodiments.
Figure 3:
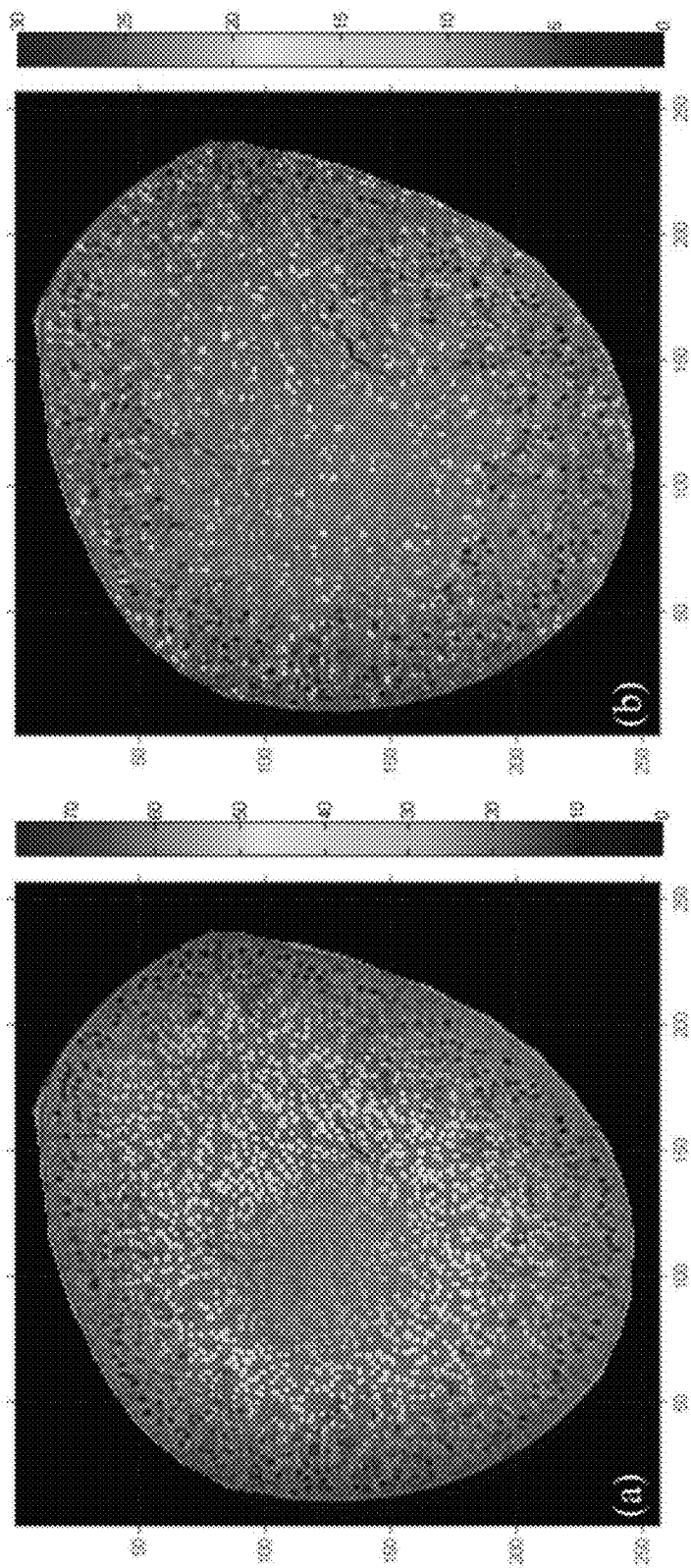
FIG. 3 illustrates (a) distance to kidney boundary information of candidate regions of an original kidney image, and (b) volume size of candidate regions, all in accordance with various exemplary embodiments.
Figure 4:
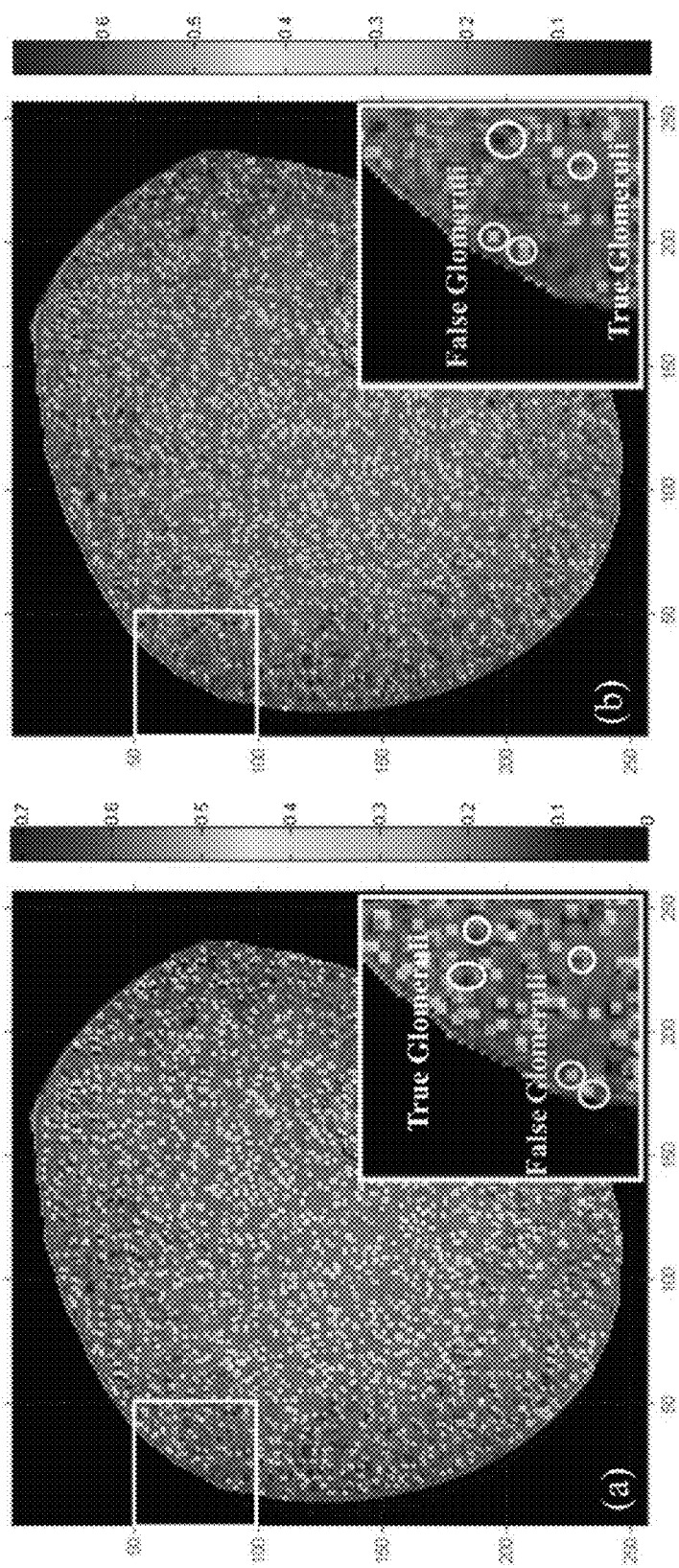
FIG. 4 illustrates (a) shape index of candidate regions of an original kidney image, and (b) Laplacian of Gaussian information of candidate regions of an original kidney image, all in accordance with various exemplary embodiments.
Figure 5:
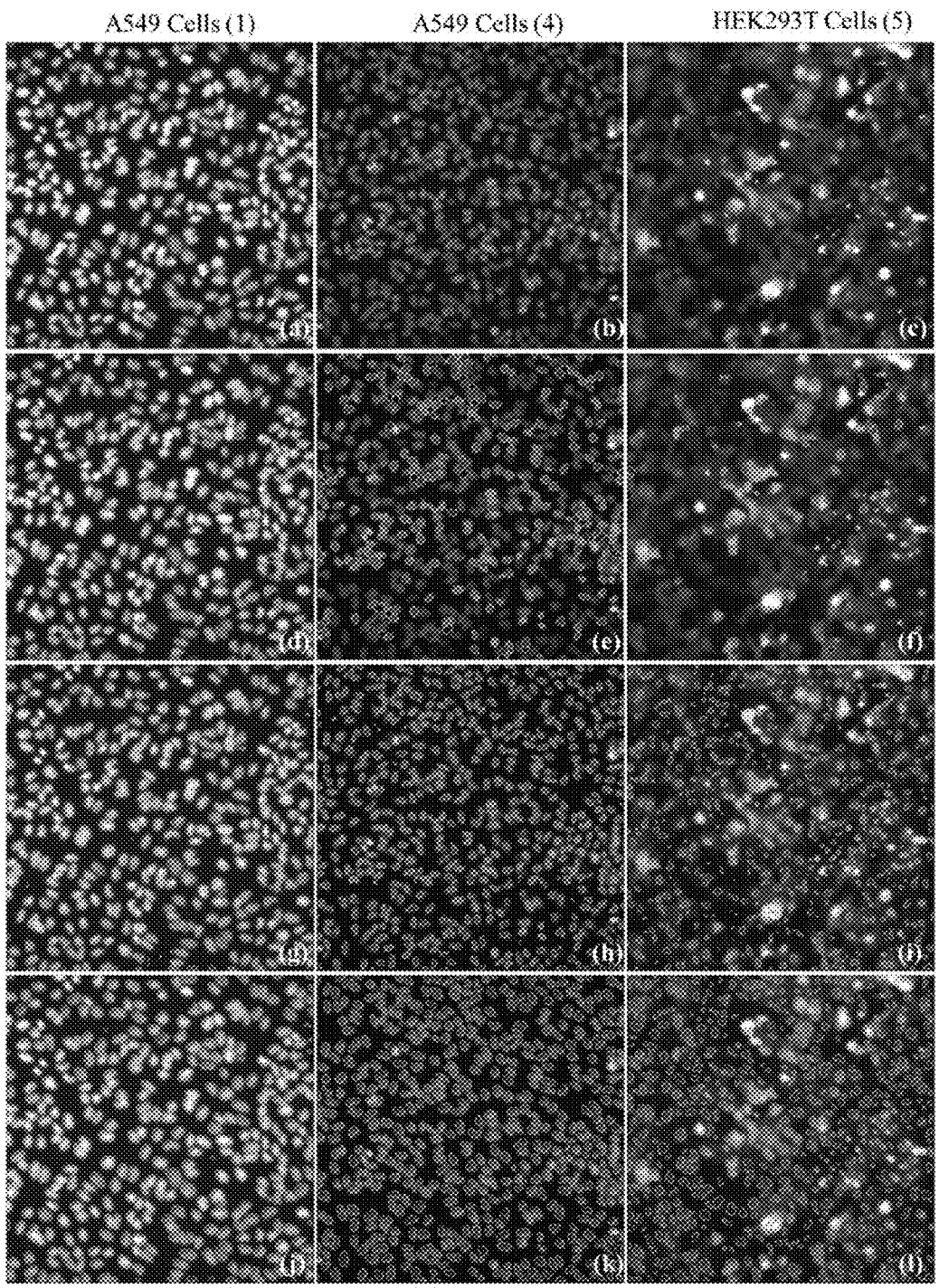
FIG. 5 illustrates results of various image processing algorithms on 2D images, showing row 1 (a)-(c): original images, row 2 (d)-(f): results of utilizing a known watershed method, row 3 (g)-(i): results of using a known graph-cut method, and row 4 (j)-(l): results of using method 100, all in accordance with various exemplary embodiments.
Figure 6:
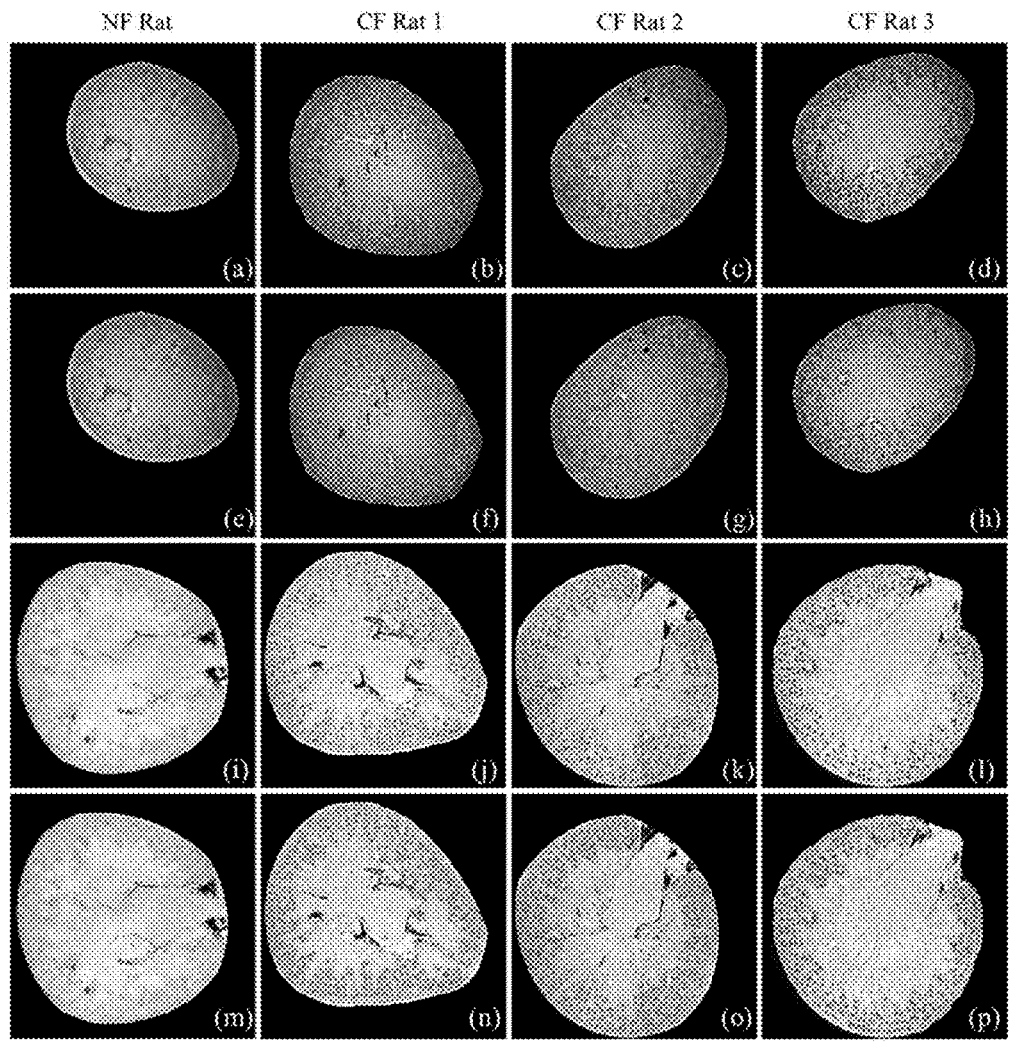
FIG. 6 illustrates operation of exemplary method 100 on rat kidney magnetic resonance imaging (MRI) images, showing row 1 (a)-(d): original images; row 2 (e)-(h): results of utilizing method 100; row 3 (i)-(l): original images, and row 4 (m)-(p): results of utilizing method 100, all in accordance with various exemplary embodiments.
Figure 7:
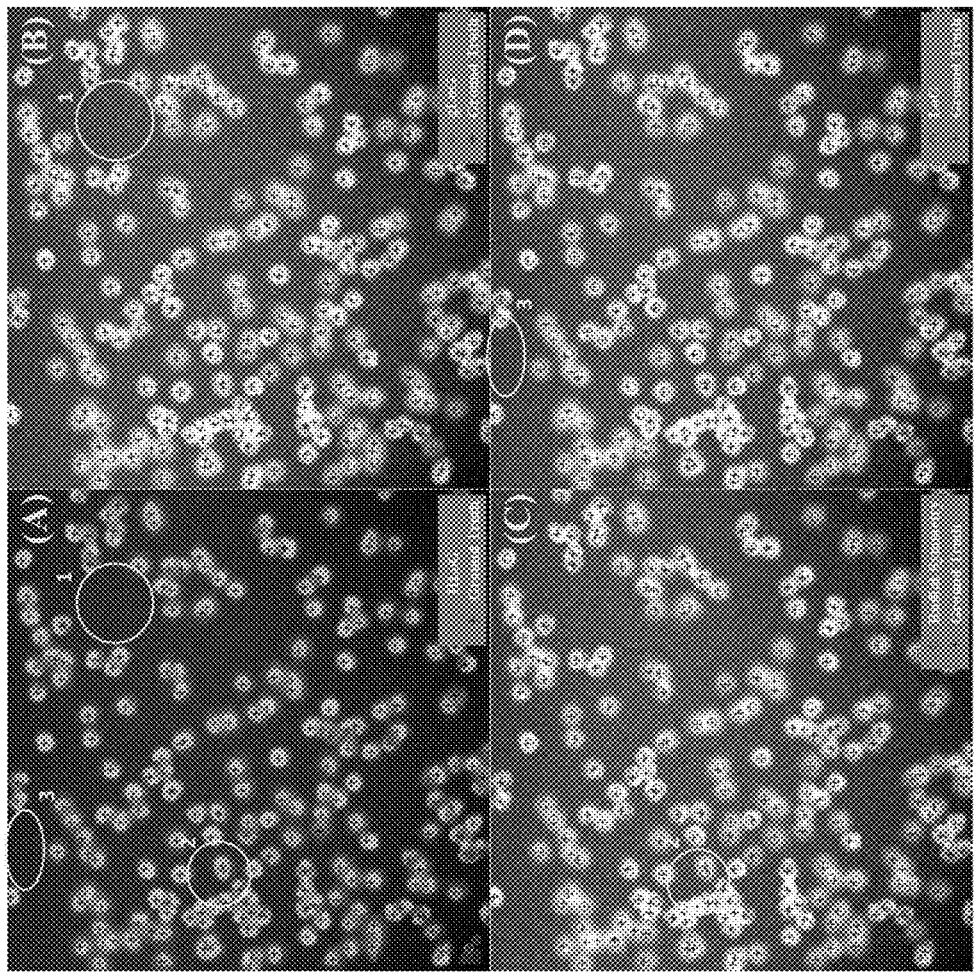
FIG. 7 illustrates results of various image processing algorithms on 2D images, showing: A) operation of method 100; B) operation of a Generalized Laplacian of Gaussian (gLoG) method; C) operation of a radial symmetry method; and D) operation of a Laplacian of Gaussian (LoG) method.

In an exemplary embodiment, with reference now to FIG. 1, a method 100 of measuring glomeruli in a kidney comprises identification of a candidate glomerular region from a 3 dimensional (3D) image of a kidney, segmentation of individual glomeruli in the 3D image of a kidney via a hessian approach (step 110), extraction of features of the individual glomeruli (step 120), and development of a model to identify the individual glomeruli in the 3D image (step 130). In accordance with an exemplary embodiment, this method may be used to detect, measure and count every glomerulus in a whole kidney ex vivo and in vivo. The features utilized in step 120 may include, but are not limited to, average intensity, divergence, distance to kidney boundary, region volume, shape index, and/or Laplacian of Gaussian (LoG).

In accordance with principles of the present disclosure, a 3 dimensional (3D) image may be generated using superparamagnetic cationic ferritin (CF) nanoparticles or other suitable method. In accordance with an exemplary embodiment, cationic ferritin nanoparticles may be used as contrast agents for MRI. CF nanoparticles bind to anionic proteoglycans in the glomerular basement membrane when injected intravenously and the accumulation of CF may be detected with T2*-weighted MRI in a 3D image.

In accordance with principles of the present disclosure, a candidate glomerular region may be identified via a suitable method, for example via a Hessian matrix-based approach. In accordance with an exemplary embodiment, a convexity property from a Hessian Matrix may be used to identify candidate glomerular regions from the whole kidney image. The convexity property may be further used to separate touching glomeruli. In an exemplary embodiment, use of the convexity property may reduce data size, allowing diverse features from each candidate glomerular object to be explored for accurate segmentation.

In various exemplary embodiments, segmentation of glomeruli may be the separation of touching glomeruli. Touching glomeruli may be glomeruli that intersect with each other in an image, forming a clump. A Hessian matrix may be applied to split the touching glomeruli based on the convexity property. The segmentation of glomeruli may allow for each individual glomeruli to be counted, providing an accurate count of glomeruli in a kidney.

In various exemplary embodiments, extraction of features of the individual glomeruli may be used. Exemplary features include, but are not limited to, one or more of average intensity $A_T$, regional blobness $R_T$, regional flatness $S_T$, average intensity (AI), divergence (Div), distance to kidney boundary (Dis), region volume(s) (Vol), shape index (SI), and Laplacian of Gaussian (LoG). In various embodiments, one or more features may be derived from domain knowledge or imaging geometrics. The application of these features may contribute to the segmentation of the glomeruli.

In accordance with principles of the present disclosure, the development of a model to identify the individual glomeruli in the 3D image may be used. In accordance with an exemplary embodiment, a model may be a Variational Bayesian Gaussian Mixture Model (VBGMM). While it will be appreciated that other models may be utilized, VBGMM may advantageously be utilized due to computational efficiency and accuracy.

In certain exemplary embodiments, a method of detecting kidney disease comprises obtaining a 3 dimensional (3D) image of a kidney, identification of a candidate glomerular region from the 3D image, segmentation of individual glomeruli in the 3D image of a kidney, and extraction of features of the individual glomeruli and development of a model to identify the individual glomeruli in the 3D image, wherein the number of glomeruli correlates with susceptibility to chronic kidney and cardiovascular disease.

It will be appreciated that Chronical Kidney Disease (CKD) develops when there are too few nephrons to maintain the homeostatic role in waste and fluid management. There are both congenital and acquired forms of nephropenia. The kidney's unique ability to adapt to fewer nephrons is reflected in the compensatory enlargement of the remaining glomeruli to maintain a constant filtration surface area and bulk glomerular filtration rate (GFR). Because of this compensatory mechanism, both endogenous and exogenous modalities that measure GFR are inadequate diagnostic tools for early detection of kidney diseases which involve changes in nephron number and glomerular volume. Studies have shown that even the mild stages of CKD are not benign and result in both higher risks of cardiovascular disease.

Exemplary results of method 100 are illustrated in FIGS. 2 through 7.

Turning now to FIGS. 8 through 12, various blob detectors have been developed over the years. These include interest point detectors such as Radial-Symmetry, SIFT, and SURF, and interest region detectors such as Harris-Affine detector, Hessian-affine detector and Hessian-Laplace detector. However, performance of these blob detectors for medical images (e.g., pathological and fluorescence images) are often unsatisfactory. Another type of detector, Laplacian of Gaussian (LoG) under the scale space theory has gained its popularity in the medical applications. In the scale space theory, one 2D image (or a slice of 3D image) is treated as a stack of images controlled by a scale parameter t. A multi-scale Gaussian scale space representation of the image is derived as the convolution of the raw image over the Gaussian kernel with respect to scale t to preserve the important spatial properties of the imaging structures. Given that as the scale parameter increases, the number of local minima in a dark blob does not increase, and the number of local maxima in a bright blob does not decrease, a diffusion process may apply to mark the identifiable blobs. For the individual blobs with similar sizes, one "optimal" scale often exists. Detectors generated via LoG kernels have been successfully applied for some blob detections. However, the symmetric nature of the LoG detector limits its applications to rotational asymmetric blobs.

This limitation has been attempted to be addressed by utilizing a generalized Laplacian of Gaussian (gLoG) in an attempt to detect rotational asymmetric structures by using different Gaussian kernels. The gLoG is thus able to detect general elliptical structures such as rotationally symmetric and asymmetric blobs. However, this approach is computationally intensive, and as such, these prior approaches are typically utilized only on 2D histopathological images and/or 2D microscopic images.

In contrast, principles of the present disclosure enable assessment, including blob detection, segmentation, and/or the like, on 3D images as well as 2D images, for example in order to segment many small structures. One challenge in 3D MR blob detection is that MR imaging is known to have acquisition noise, partial volume effect (the mixture of several tissue signals in a voxel) and bias field (spatial intensity inhomogeneity). Additionally, to enable high-throughput in vivo studies, a highly efficient detector is desirable. In addition, unlike the situation in histological sections, the glomeruli's small size corresponds to a high spatial frequency typically close to that of image noise. Thus, the segmentation is sensitive to local noises. For example, the average volume of rat glomeruli is approximately 6 to $7*10^5$ um$^3$, which is less than 10 voxels with a resolution of 62×62×62 μm$^3$ in a 3D MR image. Accordingly, exemplary methods disclosed herein provide a robust detector tolerable to image noises.

Figure 8:
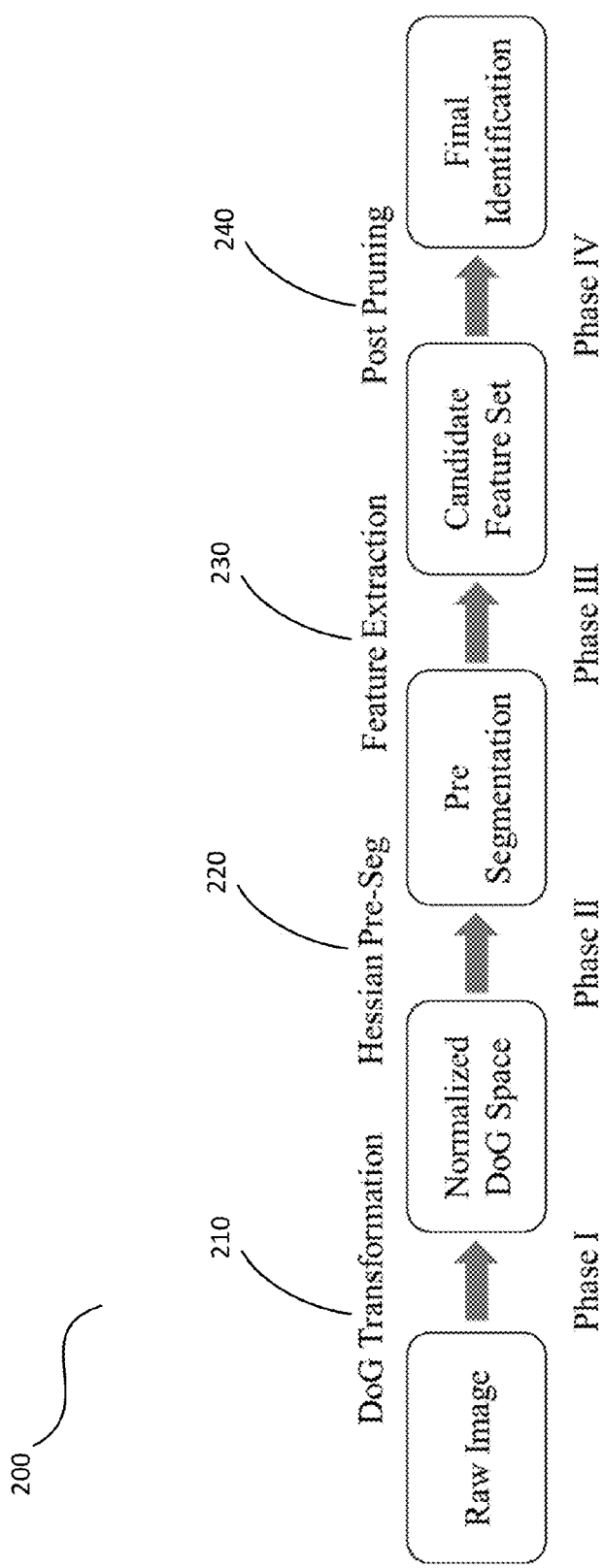
FIG. 8 illustrates an exemplary method 200 for identifying glomeruli in accordance with various exemplary embodiments.

To address these and other outstanding challenges, a Hessian-based Difference of Gaussian (HDoG) detector is disclosed. The exemplary detector improves the detectability of glomeruli in 3D. HDoG utilizes a Difference of Gaussians (DoG) approach which has great computational advantages over LoG by using the approximation of LoG in the detection process. With reference now to FIG. 8, in an exemplary HDoG method 200, a DoG transformation of a raw image that enhances the blob structures and smoothes the local noises is first obtained (step 210). Hessian analysis is then applied on the transformed imaging matrix to pre-segment and delineate the blob (glomeruli) candidates (step 220). For each glomerular candidate identified by the Hessian analysis, exemplary regional features are derived (step 230), for example average intensity feature $A_T$, regional blobness $R_T$, and regional flatness $S_T$. These features are fed to an exemplary tuning-free unsupervised clustering algorithm, for example a Variational Bayesian Gaussian mixture model (VBGMM) for post pruning (step 240).

Exemplary method 200 may be validated, for example using precision, recall and F-score metrics. In an exemplary validation test of 15 pathological images and 200 2D fluorescence microscopy cell images, HDoG outperforms both LoG and gLoG detectors with less computing time. Additionally, results on human and rat kidney images confirm that HDoG is able to segment glomeruli automatically and accurately.

In various exemplary embodiments, utilization of method 200 provides a computationally efficient approach for identifying potential glomeruli. In an exemplary embodiment, method 200 was implemented on a Windows PC configured with an Intel Xeon processor operating at 2.0 Ghz and with 32 G of RAM. An exemplary set of 15 600×800 pathologic images were processed via method 200. The average operational time of method 200 was about 9.4 seconds per image. By way of comparison, an exemplary prior method, gLoG, exhibited an average operation time of about 30 seconds per image to process the same set of 15 images. Similarly, method 200 was utilized to process 200 256×256 fluorescence-light microscopy images of cells, and achieved an average operational time of about 1.0 seconds per image. The exemplary prior method, gLoG, exhibited an average operation time of about 10.0 seconds per image. Stated another way, method 200 offers many hundreds of percent improvements in computational efficiencies over prior widely-accepted methods.

In method 200, a glomerulus may be considered as a blob, i.e., a region that is darker than surrounding, and the convexity of intensity function within a blob considered to be consistent. Yet in reality, the convex property of intensity function within a blob region may have discontinuities due to the image noise. Accordingly, it is desirable to apply a smoothing process to filter the noise and make the blob region asymptotic convex (or concave). A DoG filter may desirably be utilized because (i) it can smooth the image noise by enhancing the objects at the selected scale, (ii) it is the approximation of a Laplacian of Gaussian (LoG) filter, which can highlight the blob structure, and (iii) it is computationally efficient while offering similar accuracy. These properties are desirable to detect/segment blobs on 3D and/or 2D images.

In method 200, let an 3D image be f: $R^3 \rightarrow R$, the scale space representation L(x, y, z; t) at point (x, y, z) with scale parameter t is the convolution of image f (x, y, z) with Gaussian kernel (x, y, z; t):

$$L(x,y,z;t)=G(x,y,z;t)*f(x,y,z) \qquad \text{(Equation 1)}$$

Where * is the convolution operator and $$G(x, y, z; t) = \frac{1}{(2\pi t^2)^{\frac{3}{2}}} \exp\left(-\frac{x^2 + y^2 + z^2}{2t^2}\right).$$

The Laplacian of L(x, y, z; t) is:

$$\nabla^2 L(x,y,z;t) = L_{xx}+L_{yy}+L_{zz} \qquad \text{(Equation 2)}$$

Since $$\frac{1}{2}\nabla^2 L(x, y, z; t) = \partial_t L(x, y, z; t),$$

we have:

$$\nabla^2 L(x, y, z; t) = \lim_{\delta t \to 0} \frac{L(x, y, z; t + \delta t) - L(x, y, z; t - \delta t)}{\delta t} \approx \qquad \text{(Equation 3)}$$
$$L(x, y, z; t + \delta t) - L(x, y, z; t - \delta t)$$

That is, $$\nabla^2 L(x,y,z;t) \approx f(x,y,z)*(G(x,y,z;t+\delta t)-G(x,y,z;t-\delta t)) \qquad \text{(Equation 4)}$$

To locate an optimal scale of blob, γ-normalization may be added to method 200 detector as a normalized LoG detector $t^\gamma \nabla^2 L(x, y, z; t)$, thus an approximation of normalized LoG may be:

$$\text{DoG}_{nor}(x,y,z;t)=t^\gamma(x,y,z)*(G(x,y,z;t+\delta t)-G(x,y,z;t-\delta t)) \qquad \text{(Equation 5)}$$

In method 200, during a normalized DoG transformation, a dark glomerular blob is converted to a bright glomerular blob and vice versa. A blob after the normalized DoG operation as may be referred to herein as a transformed blob. Exemplary discussion herein focuses on a dark blob (i.e., a transformed bright blob), and it will be appreciated that a similar process may be utilized for a bright blob (i.e., a transformed dark blob).

In various exemplary embodiments, in method 200 the eigenvalues of the Hessian matrix of a blob-like structure can be used to describe the structure's geometry. After a target image is smoothed via DoG, then for any voxel (x, y, z) in the normalized DoG image $DoG_{nor}(x, y, z; t)$ at scale t, the Hessian Matrix for this voxel is:

In prior approaches, classical geometric features in blob detection are $R_B$ (the likelihood of blobness) and $S_B$ (flatness—the second order structureness). These features are based on solving eigenvalues (assuming $|\lambda_1| \leq |\lambda_2| \leq |\lambda_3|$) of Hessian at each voxel. That is, $$H(DoG_{nor}(x, y; t)) = \begin{bmatrix} \frac{\partial^2 DoG_{nor}(x, y, z; t)}{\partial x^2} & \frac{\partial^2 DoG_{nor}(x, y, z; t)}{\partial x \partial y} & \frac{\partial^2 DoG_{nor}(x, y, z; t)}{\partial x \partial z} \\ \frac{\partial^2 DoG_{nor}(x, y, z; t)}{\partial x \partial y} & \frac{\partial^2 DoG_{nor}(x, y, z; t)}{\partial y^2} & \frac{\partial^2 DoG_{nor}(x, y, z; t)}{\partial y \partial z} \\ \frac{\partial^2 DoG_{nor}(x, y, z; t)}{\partial x \partial z} & \frac{\partial^2 DoG_{nor}(x, y, z; t)}{\partial y \partial z} & \frac{\partial^2 DoG_{nor}(x, y, z; t)}{\partial z^2} \end{bmatrix}$$ (Equation 6)

Since the transformed-bright blob is concave elliptic in shape (i.e., brightness is faded isotropically), every voxel within the blob is concave elliptic. Accordingly, method 200 may apply the proposition that in a transformed 3D normalized DoG image, every voxel of a transformed-bright blob has a negative definite Hessian. This is because, given geometric classification as a voxel and specific orientation patterns, if voxel (x, y, z) is concave elliptic, all of the eigenvalues $\lambda_1, \lambda_2, \lambda_3$ of H(x, y; t) are negative, meaning $\lambda_1 < 0$, $\lambda_2 < 0$ and $\lambda_3 < 0$. Since every voxel in the transformed-bright blob is concave elliptic, its eigenvalues are all negative, and thus the Hessian matrix of the voxel is negative definite.

If a voxel resides in a transformed-bright blob, the Hessian matrix of the voxel is negative definite. But a voxel having negative definite Hessian may not be from a transformed-bright blob. Therefore, method 200 may utilize the following definition: a blob candidate T in normalized DoG space is a 6-connected component of set U={(x, y, z)|(x, y, z)∈ $DoG_{nor}(x, y, z; t)$, I(x, y, z; t)=1}, where I(x, y, z; t) is the binary indicator such that if the voxel (x, y, z) has a negative definite Hessian then I(x, y, z; t)=1, otherwise I(x, y, z; t)=0.

$$R_B = \frac{\text{Volume of Blob}/(4\pi/3)}{(\text{Largest Cross section}/\pi)^{3/2}} = \frac{|\lambda_1|}{\sqrt{|\lambda_2 \lambda_3|}}$$ (Equation 7)

$$S_B = \sqrt{\lambda_1^2 + \lambda_2^2 + \lambda_3^2}$$ (Equation 8)

Because the eigenvalues $\lambda_1, \lambda_2, \lambda_3$ indicate the magnitudes of corresponding orthogonal curvatures represented by eigenvectors of Hessian, $R_B$ describes the likelihood of the blob-like structure, and can attain maximum 1 when the region is an idealized blob. $S_B$ describes the deviation of the three orthogonal curvatures from "flat". The higher value $S_B$ is, the stronger contrast can be achieved of the blob region against the background.

However, to calculate $R_B$, eigenvalues of Hessian need to be solved at each voxel. This procedure requires intensive computations. Accordingly, in order to improve computational efficiency, method 200 utilizes a new approach where modified features $R_T$ and $S_T$ are utilized. These two features are built upon regional Hessian evaluated at each glomerular candidate T instead of each voxel. The regional Hessian over the DoG transformation (smoothed images) is defined as $$H_T(DoG_{nor}(x, y; t)) = \sum_{(x,y,z) \in T} \begin{bmatrix} \frac{\partial^2 DoG_{nor}(x, y, z; t)}{\partial x^2} & \frac{\partial^2 DoG_{nor}(x, y, z; t)}{\partial x \partial y} & \frac{\partial^2 DoG_{nor}(x, y, z; t)}{\partial x \partial z} \\ \frac{\partial^2 DoG_{nor}(x, y, z; t)}{\partial x \partial y} & \frac{\partial^2 DoG_{nor}(x, y, z; t)}{\partial y^2} & \frac{\partial^2 DoG_{nor}(x, y, z; t)}{\partial y \partial z} \\ \frac{\partial^2 DoG_{nor}(x, y, z; t)}{\partial x \partial z} & \frac{\partial^2 DoG_{nor}(x, y, z; t)}{\partial y \partial z} & \frac{\partial^2 DoG_{nor}(x, y, z; t)}{\partial z^2} \end{bmatrix}$$ (Equation 9)

In various exemplary embodiments, in method 200 definiteness of the Hessian can be assessed by the leading principal minors instead of calculating its eigenvalues of the matrix. Specifically, if $D_k$ is the k-th leading principal minor of matrix M, we conclude it is negative definite if and only if $(-1)^k D_k > 0$.

Figure 9:
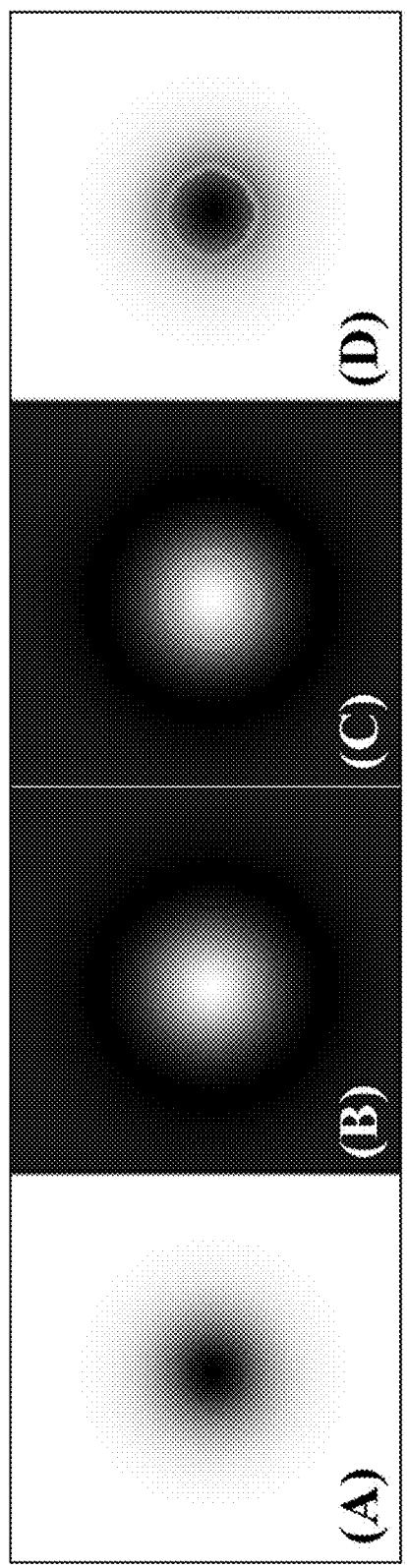
FIG. 9 illustrates operation of a Hessian pre-segmentation on an idealized blob in accordance with various exemplary embodiments.
Figure 10:
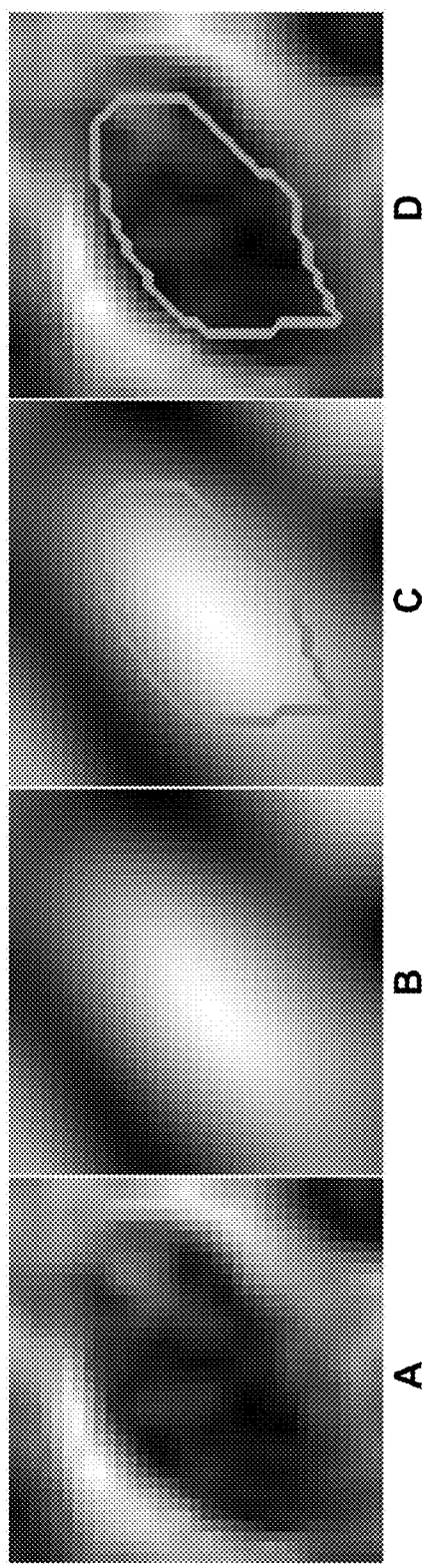
FIG. 10 illustrates operation of a Hessian pre-segmentation on a blob in accordance with various exemplary embodiments.
Figure 11B:
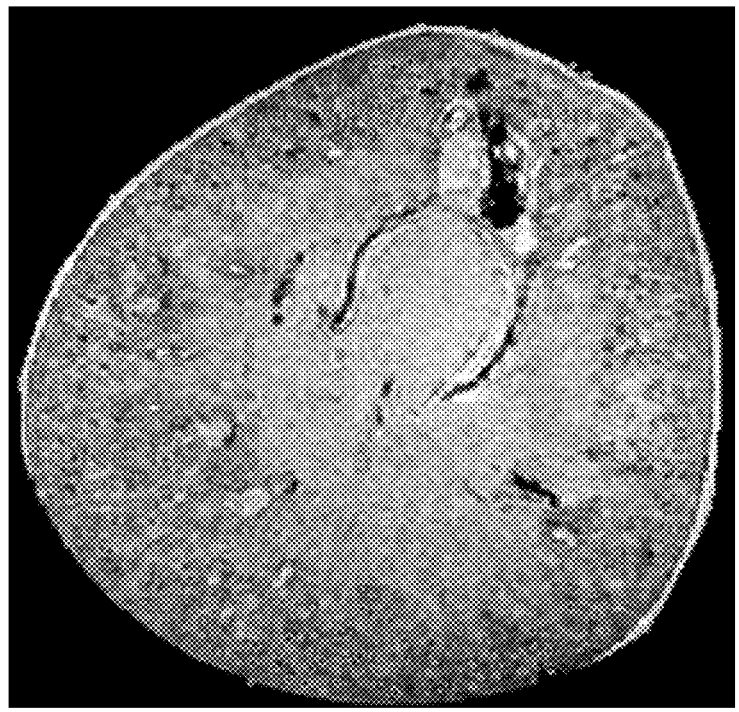
FIGS. 11A and 11B illustrate operation of an exemplary method for identifying glomeruli, showing in 11A an original image, and in 11B the image after processing, highlighting glomeruli candidates, all in accordance with various exemplary embodiments.
Figure 11A:
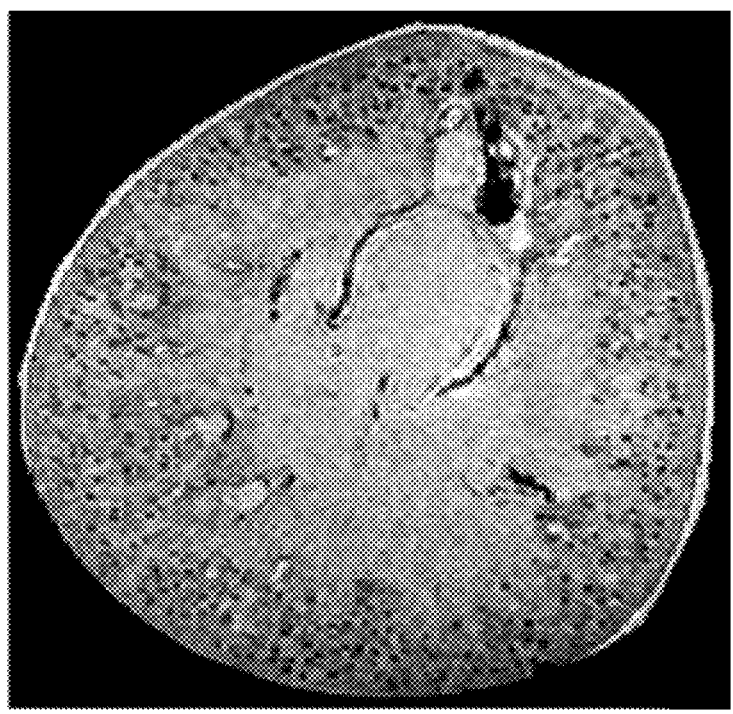
Figure 12A:
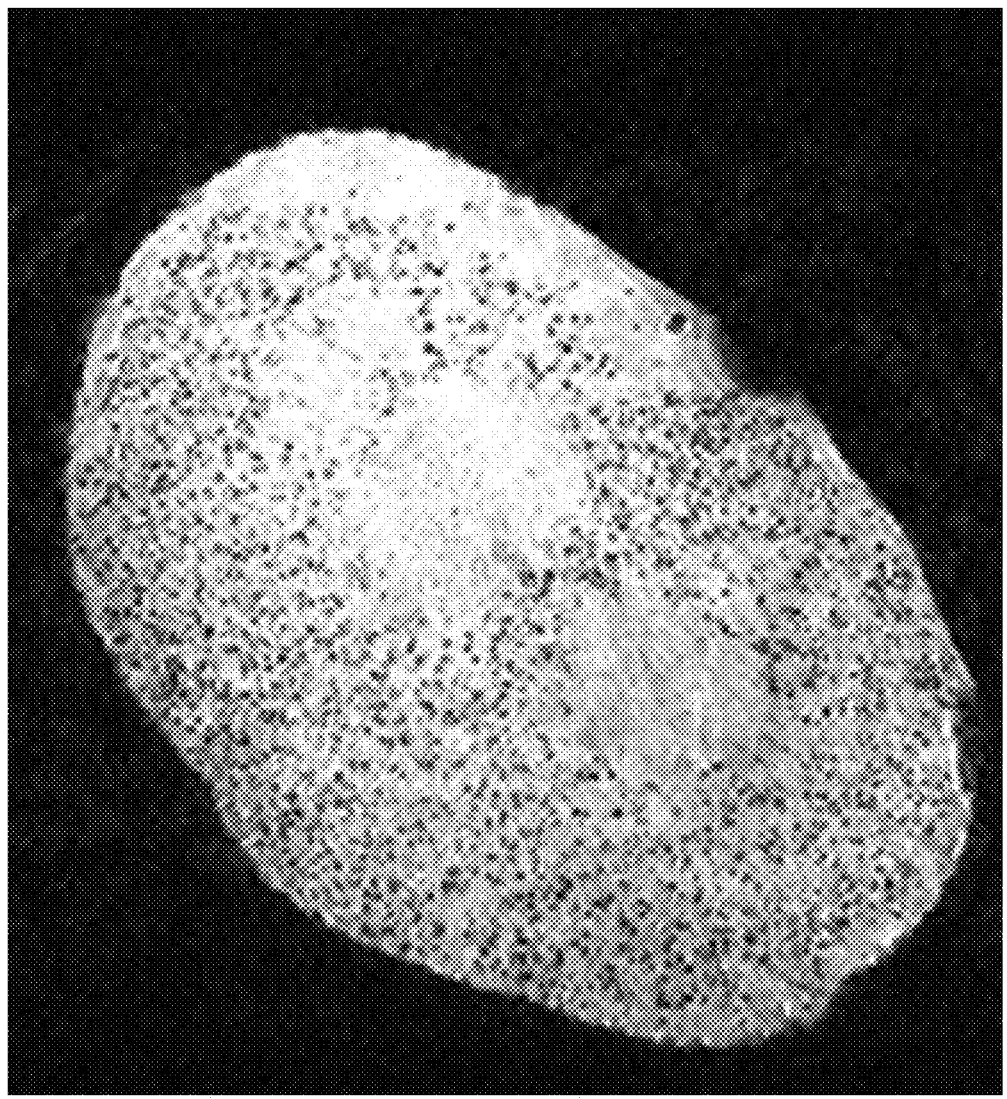
FIGS. 12A and 12B illustrate operation of an exemplary method for identifying glomeruli, showing in 12A an original image, and in 12B the image after processing, highlighting glomeruli candidates, all in accordance with various exemplary embodiments.
Figure 12B:
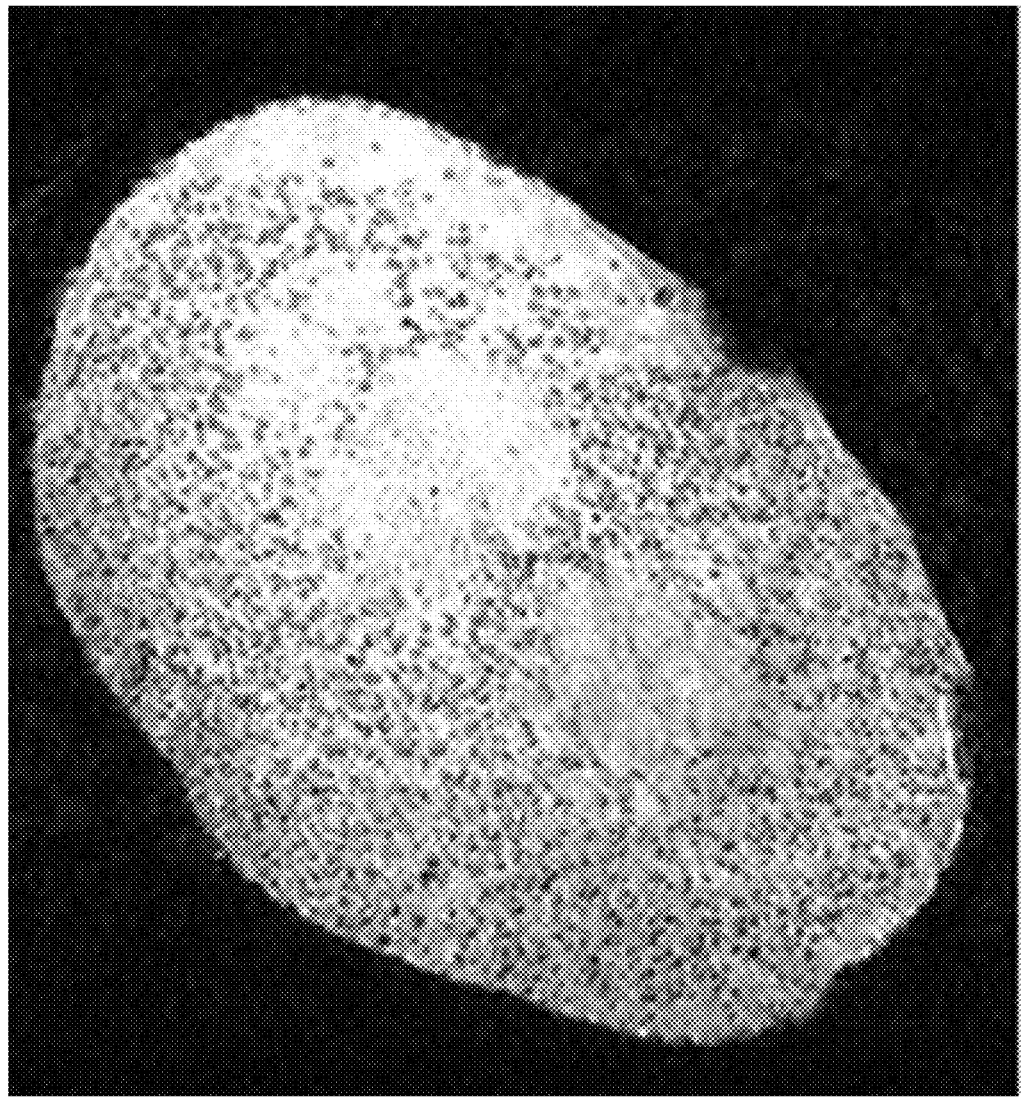

As illustrated in FIGS. 9 and 10, application of step 220 not only detects glomeruli candidates (usually, a set of all true glomeruli with some false identifications), but also delineates the boundary of each glomeruli candidate.

Equation 9 is the summation of Hessian matrix over candidate region T. In an exemplary embodiment, this matrix describes the second-order derivative distribution within the region of the blob candidate. The derivatives are equally weighted averaged (sum over the region T) at the centroid of T over the region. The eigenvalues of this matrix represent the three principal curvatures of the centroid over the blob candidate, and can be utilized to measure the blobness over the region.

To efficiently measure the likelihood of blobness, a modified version of Equation (7) is utilized as:

$$R_T = \cfrac{1}{\left(\cfrac{(xy \text{ plane Cross section}/\pi)}{(\text{Volume of blob}/(4\pi/3))^{2/3}} + \cfrac{(xz \text{ plane Cross section}/\pi)}{(\text{Volume of blob}/(4\pi/3))^{2/3}} + \cfrac{(yz \text{ plane Cross section}/\pi)}{(\text{Volume of blob}/(4\pi/3))^{2/3}}\right)/3} = \cfrac{3 \times |\lambda_1' \lambda_2' \lambda_3'|^{\frac{2}{3}}}{|\lambda_1' \lambda_2'| + |\lambda_2' \lambda_3'| + |\lambda_1' \lambda_3'|} \quad \text{(Equation 10)}$$

In Equation 10, $\lambda'_1$, $\lambda'_2$, $\lambda'_3$ are eigenvalues of regional Hessian $H_T$. Since the Hessian matrix is negative definite at every voxel within a blob candidate, the sum of the Hessian matrix over a blob candidate is negative definite, meaning $\lambda'_1, \lambda'_2, \lambda'_3 < 0$. Thus, we have $$R_T = \frac{3 \times |\lambda_1' \lambda_2' \lambda_3'|^{\frac{2}{3}}}{\lambda_1' \lambda_2' + \lambda_2' \lambda_3' + \lambda_1' \lambda_3'} = \frac{3 \times tr(H_T)^{\frac{2}{3}}}{pm(H_T)} \quad \text{(Equation 11)}$$

where $pm(H_T) = \lambda_1'\lambda_2' + \lambda_2'\lambda_3' + \lambda_1'\lambda_3'$. Additionally, $pm(H_T)$ can be obtained by calculating three 2 by 2 principal minors of $H_T$, that is $$\lambda_1' \lambda_2' + \lambda_2' \lambda_3' + \lambda_1' \lambda_3' = \quad \text{(Equation 12)}$$
$$\det\begin{pmatrix} H_T^{1,1} & H_T^{1,2} \\ H_T^{2,1} & H_T^{2,2} \end{pmatrix} + \det\begin{pmatrix} H_T^{2,2} & H_T^{2,3} \\ H_T^{3,2} & H_T^{3,3} \end{pmatrix} + \det\begin{pmatrix} H_T^{1,1} & H_T^{1,3} \\ H_T^{3,1} & H_T^{3,3} \end{pmatrix}$$

In method 200, to calculate the flatness over blob candidate T, we can utilize:

$$S_T = \sqrt{(\lambda_1' + \lambda_2' + \lambda_3')^2 - 2(\lambda_1'\lambda_2' + \lambda_2'\lambda_3' + \lambda_1'\lambda_3')} = \quad \text{(Equation 13)}$$
$$\sqrt{tr(H_T)^2 - 2 \times pm(H_T)}$$

In method 200, modified features $R_T$ and $S_T$ greatly reduce the computational burden as compared to prior approaches (illustrated in Eq. (7) and Eq. (8)) in that: (1) $R_T$ and $S_T$ are based on the regional Hessian evaluated at each blob region instead of at every voxel, and (2) $R_T$ and $S_T$ only require the calculations of trace and determinant, instead of requiring to find the roots (eigenvalues) of the characteristic equation of the Hessian matrix in Eq. (7) and Eq. (8). In method 200, $R_T$ and $S_T$ may be utilized together with the feature $A_T$, the average intensity value over region T. In various exemplary embodiments, these three features are input to a clustering algorithm, for example a Variational Bayesian Gaussian Mixture Model, to reduce and/or remove false identifications from the glomeruli candidate pool.

In various exemplary embodiments, method 200 utilizes a post pruning approach (step 240) in order to eliminate false glomeruli candidates. In method 200, a Variational Bayesian Gaussian Mixture Model (VBGMM) may be utilized because: (1) compared to the maximum likelihood Gaussian Mixture Model, the variational model is free from being trapped to a singularity solution; and (2) the variational model is able to automatically identify the number of clusters for optimum performance without the need for initialization and subjective parameter settings. In the VBGMM, given a 3D MR image, it can be considered that several multivariate Gaussian distribution components form the entire image. One of the components is a group of glomeruli, with others belonging to the background and image noises. In method 200, $X = \{X^1, \ldots, X^N\}$ is the observation, and $N(X^i|\mu, \Lambda)$ is the multivariate Gaussian distribution with mean $\mu$ and inverse covariance $\Lambda$ that $X^i$ follows. The mixture distribution for M components is:

$$P(X^i|\pi,\mu,\Lambda) = \Sigma_{j=1}^M \pi_j N(X^i|\mu,\Lambda) \quad \text{(Equation 14)}$$

where $\pi_j$ is the weight for component j.

In method 200, the elements in X may be assumed to be independent to each other, and a binary latent variable, $Z = \{Z^1, \ldots, Z^{NM}\}$ where $z_{im} = 1$ may be introduced. This indicates that $X^i$ belongs to class m and $\Sigma_{j=1}^M Z^{ij} = 1$. The conditional probability of the image data set is:

$$P(X|Z,\mu,\Lambda) = \Pi_{i=1}^N \Pi_{j=1}^M N(X^i|\mu,\Lambda)^{Z^{ij}} \quad \text{(Equation 15)}$$

In method 200, the variational Bayesian Gaussian Mixture model can approximate the posterior $P(\theta|X)$ given any distribution $P(X)$ and unknown parameters $\theta$, by a simpler distribution $Q(\theta)$ that marginalizes the unknown parameter $\theta$. In various exemplary embodiments, observation $X^i$ is a vector of three features $A_T$, $R_T$, $S_T$ for a glomerular candidate region. The observations (glomerular candidate regions) form a multivariate Gaussian mixture and therefore they can be clustered into glomerular regions and non-glomerular regions, for example by using a Bayesian inference method.

Validation of method 200 may be conducted against known results on known images, for example a set of 15 pathological images with known results. The comparison result is shown in Table 1.

TABLE 1

COMPARISON RESULTS OF METHOD 200, GLOG
AND LOG ON 15 PATHOLOGIC IMAGES.

|   | Method 200 (Avg ± Std) | | | gLoG (Avg ± Std) | | | LoG (Avg ± Std) | | |
|---|---|---|---|---|---|---|---|---|---|
| d | Precision | Recall | Fscore | Precision | Recall | Fscore | Precision | Recall | Fscore |
| 0 | 0.042 ± 0.010 | 0.044 ± 0.011 | 0.043 ± 0.010 | 0.046 ± 0.010 | 0.047 ± 0.009 | 0.046 ± 0.010 | 0.040 ± 0.008 | 0.043 ± 0.008 | 0.041 ± 0.008 |
| 1 | 0.171 ± 0.020 | 0.178 ± 0.020 | 0.174 ± 0.020 | 0.192 ± 0.032 | 0.196 ± 0.026 | 0.193 ± 0.028 | 0.168 ± 0.027 | 0.177 ± 0.026 | 0.172 ± 0.026 |
| 2 | 0.346 ± 0.048 | 0.359 ± 0.045 | 0.352 ± 0.046 | 0.399 ± 0.053 | 0.407 ± 0.038 | 0.402 ± 0.045 | 0.338 ± 0.041 | 0.359 ± 0.048 | 0.348 ± 0.042 |

TABLE 1-continued

COMPARISON RESULTS OF METHOD 200, GLOG AND LOG ON 15 PATHOLOGIC IMAGES.

| | Method 200 (Avg ± Std) | | | gLoG (Avg ± Std) | | | LoG (Avg ± Std) | | |
|---|---|---|---|---|---|---|---|---|---|
| d | Precision | Recall | Fscore | Precision | Recall | Fscore | Precision | Recall | Fscore |
| 3 | 0.548 ± 0.059 | 0.569 ± 0.051 | 0.558 ± 0.054 | 0.610 ± 0.064 | 0.624 ± 0.042 | 0.616 ± 0.051 | 0.517 ± 0.059 | 0.548 ± 0.064 | 0.531 ± 0.058 |
| 4 | 0.666 ± 0.060 | 0.692 ± 0.047 | 0.679 ± 0.052 | 0.729 ± 0.065 | 0.746 ± 0.038 | 0.737 ± 0.048 | 0.618 ± 0.057 | 0.655 ± 0.064 | 0.634 ± 0.055 |
| 5 | 0.759 ± 0.053 | 0.789 ± 0.036 | 0.773 ± 0.041 | 0.807 ± 0.059 | 0.827 ± 0.029 | 0.816 ± 0.039 | 0.684 ± 0.057 | 0.726 ± 0.063 | 0.703 ± 0.052 |
| 6 | 0.801 ± 0.048 | 0.833 ± 0.028 | 0.816 ± 0.033 | 0.840 ± 0.054 | 0.861 ± 0.024 | 0.849 ± 0.032 | 0.718 ± 0.054 | 0.762 ± 0.063 | 0.738 ± 0.048 |
| 7 | 0.833 ± 0.045 | 0.866 ± 0.024 | 0.849 ± 0.028 | 0.857 ± 0.050 | 0.879 ± 0.023 | 0.867 ± 0.026 | 0.740 ± 0.050 | 0.785 ± 0.062 | 0.760 ± 0.045 |
| 8 | 0.853 ± 0.041 | 0.887 ± 0.024 | 0.869 ± 0.025 | 0.870 ± 0.048 | 0.893 ± 0.024 | 0.880 ± 0.023 | 0.757 ± 0.048 | 0.803 ± 0.063 | 0.777 ± 0.043 |
| 9 | 0.867 ± 0.038 | 0.903 ± 0.021 | 0.884 ± 0.020 | 0.881 ± 0.046 | 0.904 ± 0.024 | 0.891 ± 0.020 | 0.769 ± 0.047 | 0.816 ± 0.062 | 0.790 ± 0.041 |
| 10 | 0.875 ± 0.036 | 0.911 ± 0.021 | 0.892 ± 0.017 | 0.887 ± 0.047 | 0.910 ± 0.024 | 0.897 ± 0.020 | 0.780 ± 0.045 | 0.827 ± 0.062 | 0.801 ± 0.039 |
| 11 | 0.881 ± 0.036 | 0.917 ± 0.022 | 0.898 ± 0.018 | 0.893 ± 0.048 | 0.916 ± 0.023 | 0.903 ± 0.020 | 0.786 ± 0.045 | 0.834 ± 0.062 | 0.807 ± 0.038 |
| 12 | 0.887 ± 0.034 | 0.923 ± 0.023 | 0.904 ± 0.016 | 0.897 ± 0.048 | 0.920 ± 0.022 | 0.907 ± 0.020 | 0.792 ± 0.045 | 0.840 ± 0.060 | 0.813 ± 0.037 |
| 13 | 0.894 ± 0.035 | 0.930 ± 0.022 | 0.911 ± 0.017 | 0.902 ± 0.048 | 0.925 ± 0.022 | 0.912 ± 0.019 | 0.798 ± 0.045 | 0.847 ± 0.058 | 0.820 ± 0.035 |
| 14 | 0.899 ± 0.037 | 0.935 ± 0.021 | 0.916 ± 0.017 | 0.907 ± 0.049 | 0.930 ± 0.022 | 0.917 ± 0.021 | 0.805 ± 0.047 | 0.854 ± 0.059 | 0.827 ± 0.036 |
| 15 | 0.905 ± 0.038 | 0.942 ± 0.019 | 0.922 ± 0.017 | 0.911 ± 0.049 | 0.935 ± 0.022 | 0.921 ± 0.021 | 0.816 ± 0.051 | 0.865 ± 0.056 | 0.838 ± 0.037 |
| 16 | 0.911 ± 0.038 | 0.948 ± 0.019 | 0.929 ± 0.017 | 0.916 ± 0.048 | 0.940 ± 0.024 | 0.927 ± 0.020 | 0.827 ± 0.055 | 0.876 ± 0.053 | 0.849 ± 0.038 |

As shown in Table 1, across all the range of d, method 200 outperforms gLoG on Recall while underperforming gLoG on precision. This leads to a comparable result of F-score on method 200 compared to gLoG (for some values of d, HDoG outperforms gLoG while for the rest values of d, gLoG outperforms HDoG). Comparing to LoG detector, method 200 provides better results on Precision, Recall and F-score for all d. In addition, the results of standard deviation show that method 200 is more robust and has fewer variations as compared to gLoG and LoG.

Another comparison result of method 200 against known results on known images (a validation dataset of 200 256× 256 fluorescence-light microscopy cell images) is shown in Table 2.

TABLE 2

COMPARISON RESULTS OF METHOD 200, GLOG ANG LOG ON 200 FLUORESCENT IMAGES.

| | Method 200 (Avg ± Std) | | | gLoG (Avg ± Std) | | | LoG (Avg ± Std) | | |
|---|---|---|---|---|---|---|---|---|---|
| d | Precision | Recall | Fscore | Precision | Recall | Fscore | Precision | Recall | Fscore |
| 0 | 0.111 ± 0.029 | 0.100 ± 0.030 | 0.105 ± 0.028 | 0.078 ± 0.032 | 0.078 ± 0.024 | 0.077 ± 0.027 | 0.067 ± 0.017 | 0.088 ± 0.027 | 0.075 ± 0.020 |
| 1 | 0.419 ± 0.057 | 0.376 ± 0.063 | 0.395 ± 0.055 | 0.322 ± 0.100 | 0.323 ± 0.050 | 0.317 ± 0.075 | 0.250 ± 0.033 | 0.325 ± 0.065 | 0.280 ± 0.038 |
| 2 | 0.740 ± 0.068 | 0.663 ± 0.067 | 0.696 ± 0.051 | 0.603 ± 0.167 | 0.606 ± 0.058 | 0.593 ± 0.115 | 0.421 ± 0.045 | 0.546 ± 0.085 | 0.471 ± 0.043 |
| 3 | 0.923 ± 0.079 | 0.825 ± 0.054 | 0.867 ± 0.038 | 0.809 ± 0.213 | 0.814 ± 0.054 | 0.796 ± 0.140 | 0.518 ± 0.057 | 0.669 ± 0.079 | 0.579 ± 0.038 |
| 4 | 0.944 ± 0.080 | 0.844 ± 0.054 | 0.887 ± 0.038 | 0.847 ± 0.220 | 0.852 ± 0.050 | 0.834 ± 0.143 | 0.546 ± 0.062 | 0.703 ± 0.073 | 0.610 ± 0.036 |
| 5 | 0.947 ± 0.080 | 0.846 ± 0.054 | 0.890 ± 0.038 | 0.850 ± 0.221 | 0.856 ± 0.051 | 0.837 ± 0.143 | 0.559 ± 0.066 | 0.719 ± 0.070 | 0.624 ± 0.037 |
| 6 | 0.947 ± 0.080 | 0.846 ± 0.054 | 0.890 ± 0.038 | 0.851 ± 0.221 | 0.857 ± 0.051 | 0.838 ± 0.143 | 0.563 ± 0.067 | 0.725 ± 0.069 | 0.628 ± 0.038 |
| 7 | 0.947 ± 0.080 | 0.846 ± 0.054 | 0.890 ± 0.038 | 0.851 ± 0.221 | 0.857 ± 0.051 | 0.838 ± 0.143 | 0.568 ± 0.069 | 0.730 ± 0.069 | 0.633 ± 0.039 |

As shown in Table 2, though the Recall on method 200 is comparable to gLoG, on Precision and F-Score, method 200 outperforms gLoG for all d. Compared to LoG, method provides better performance on all three metrics: Precision, Recall and F-Score across the range of d. Additionally, method 200 has the least variations and thus is quite robust.

Method 200 may be validated by operation on human kidney images, as shown in Table 3:

TABLE 3

GLOMERULAR COUNTS OBTAINED FOR THREE HUMAN KIDNEYS USING METHOD 200 AND STEREOLOGY

| Subject | Method 200 | | Stereology |
|---|---|---|---|
| | Glomeruli Count | Processing Time (s) | Glomeruli Count |
| Human CF1 | 1,242,008 | 13316.6 | 1,130,000 |
| Human CF2 | 711,397 | 3301.7 | 740,000 |
| Human CF3 | 1,370,095 | 3159.4 | 1,460,000 |
| Avg | 1,107,833 | 6592.567 | 1,110,000 |
| Std | 349,246 | 5823.618 | 360,416 |

Exemplary results of method 200 are illustrated in FIGS. 11A through 12B. Additional details regarding certain exemplary principles of the present disclosure, for example methods 100 and/or 200, may be found in M. Zhang et al., "Small Blob Identification in Medical Images Using Regional Features from Optimum Scale" published in *IEEE Transactions on Biomedical Engineering*, Vol. PP, Issue 99 on Sep. 25, 2014, the contents of which are incorporated herein by reference in their entirety.

It will be appreciated that, while principles of the present disclosure have been discussed in terms of kidneys and glomeruli, such principles may desirably be applied to other organs and/or disorders, for example those wherein blob detection is desirable.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure and may be expressed in the following claims.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method of measuring glomeruli in a kidney, the method comprising:
    obtaining a 3 dimensional image of a kidney;
    smoothing the image via a Difference of Gaussians filter;
    conducting a Hessian analysis on the smoothed image to mark glomeruli candidates;
    identifying, for each glomeruli candidate, average intensity $A_T$, likelihood of blobness $R_T$, and flatness $S_T$; and
    executing a clustering algorithm to post prune the glomeruli candidates, wherein the clustering algorithm evaluates, for each glomeruli candidate, the average intensity $A_T$, the likelihood of blobness $R_T$, and the flatness $S_T$ to determine if a glomeruli candidate should be counted as a true glomeruli,
    wherein $$R_T = \frac{3 \times |\lambda_1' \lambda_2' \lambda_3'|^{\frac{2}{3}}}{\lambda_1' \lambda_2' + \lambda_2' \lambda_3' + \lambda_1' \lambda_3'},$$

and
    wherein $\lambda_1'$, $\lambda_2'$, $\lambda_3'$ are eigenvalues of a regional Hessian $H_T$.

2. The method of claim 1, wherein the clustering algorithm is a Variational Bayesian Gaussian Mixture Model.

3. The method of claim 2, wherein the Variational Bayesian Gaussian Mixture Model automatically identifies a number of clusters for optimum performance of the clustering algorithm without the need for initialization and subjective parameter settings.

4. The method of claim 1, wherein the 3 dimensional image is a magnetic resonance imaging (MRI) image.

5. The method of claim 1, further comprising utilizing the output of the clustering algorithm to evaluate the susceptibility of an individual to chronic kidney and/or cardiovascular disease.

6. The method of claim 1, wherein the Hessian analysis delineates the boundary of each glomeruli candidate.

7. The method of claim 1, wherein $$S_T = \sqrt{(\lambda_1' + \lambda_2' + \lambda_3')^2 - 2(\lambda_1'\lambda_2' + \lambda_2'\lambda_3' + \lambda_1'\lambda_3')}.$$

8. The method of claim 1, further comprising extracting features of the individual glomeruli candidates.

9. The method of claim 8, wherein the features comprise at least one of average intensity, divergence, distance to kidney boundary, region volume, shape index, or Laplacian of Gaussian (LoG).

10. The method of claim 1, wherein the identifying, for each glomeruli candidate, the likelihood of blobness $R_T$ and the flatness $S_T$ utilizes a calculation of trace and determinant of the regional Hessian $H_T$.

* * * * *